(12) United States Patent
Dörr et al.

(10) Patent No.: US 7,764,987 B2
(45) Date of Patent: Jul. 27, 2010

(54) SIGNAL PROCESSING APPARATUS FOR PHYSIOLOGICAL SIGNALS

(75) Inventors: Thomas Dörr, Berlin (DE); Ingo Weiss, Berlin (DE); Peter Schneider, Berlin (DE)

(73) Assignee: Biotronik CRM Patent AG (CH)

( * ) Notice: Subject to any disclaimer, the term of this patent is extended or adjusted under 35 U.S.C. 154(b) by 771 days.

(21) Appl. No.: 11/218,303

(22) Filed: Sep. 1, 2005

(65) Prior Publication Data

US 2006/0047216 A1    Mar. 2, 2006

(30) Foreign Application Priority Data

Sep. 2, 2004    (DE) ................... 10 2004 043 005

(51) Int. Cl.
*A61B 5/0428*    (2006.01)
(52) U.S. Cl. .................................... 600/509
(58) Field of Classification Search ............... 600/508, 600/509, 515–518
See application file for complete search history.

(56) References Cited

U.S. PATENT DOCUMENTS

| | | | |
|---|---|---|---|
| 4,193,393 A | | 3/1980 | Schlager |
| 4,680,708 A | * | 7/1987 | Ambos et al. ............... 600/509 |
| 5,433,209 A | | 7/1995 | Gallant et al. |
| 5,560,369 A | | 10/1996 | McClure et al. |
| 5,836,889 A | | 11/1998 | Wyborny et al. |
| 2002/0128564 A1 | | 9/2002 | Carlson et al. |
| 2002/0193696 A1 | | 12/2002 | Hsu et al. |
| 2005/0033368 A1 | | 2/2005 | Fishler et al. |

FOREIGN PATENT DOCUMENTS

| | | |
|---|---|---|
| DE | 69329710 | 2/1995 |
| DE | 10163348 | 7/2003 |
| EP | 0 760 225 | 3/1997 |

OTHER PUBLICATIONS

Bernd Nowak, "Pacemaker Stored Electrograms: Teaching Us What Is Really Going On in Our Patients", Journal of Pacing and Clinical Electrophysiology, vol. 25, No. 5, May 2002, pp. 838-849.

* cited by examiner

*Primary Examiner*—George R Evanisko
(74) *Attorney, Agent, or Firm*—Hahn Loeser & Parks LLP

(57) ABSTRACT

A signal processing apparatus is disclosed comprising an input stage for the preparation of a physiological signal, in particular an electrocardiogram, which is adapted to provide a signal of an alternating polarity, which is formed from the physiological signal and which is to be evaluated, and is connected to an evaluation stage for forwarding of the signal to be evaluated, wherein the evaluation stage is adapted to respond to a reference moment in time associated with the physiological signal, and for at least one signal segment, associated in respect of time with the reference moment in time, of the signal to be evaluated, to detect a respective amplitude value for at least some characteristic curve points contained in the signal segment such as signal maxima and minima, inflection points and so forth and to generate from the amplitude values obtained in that way a morphology code which describes the form of the respective signal segment.

22 Claims, 16 Drawing Sheets

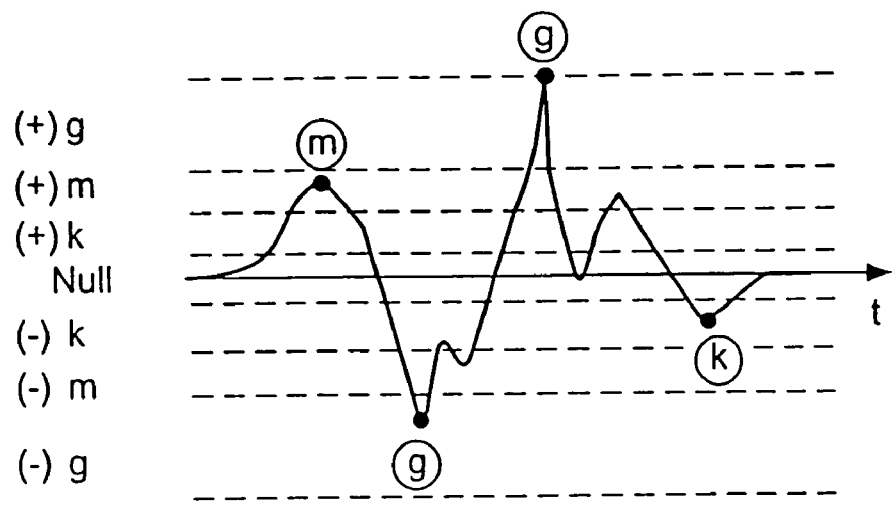
- significant signal spikes
Fig.1   Establishing significant signal spikes
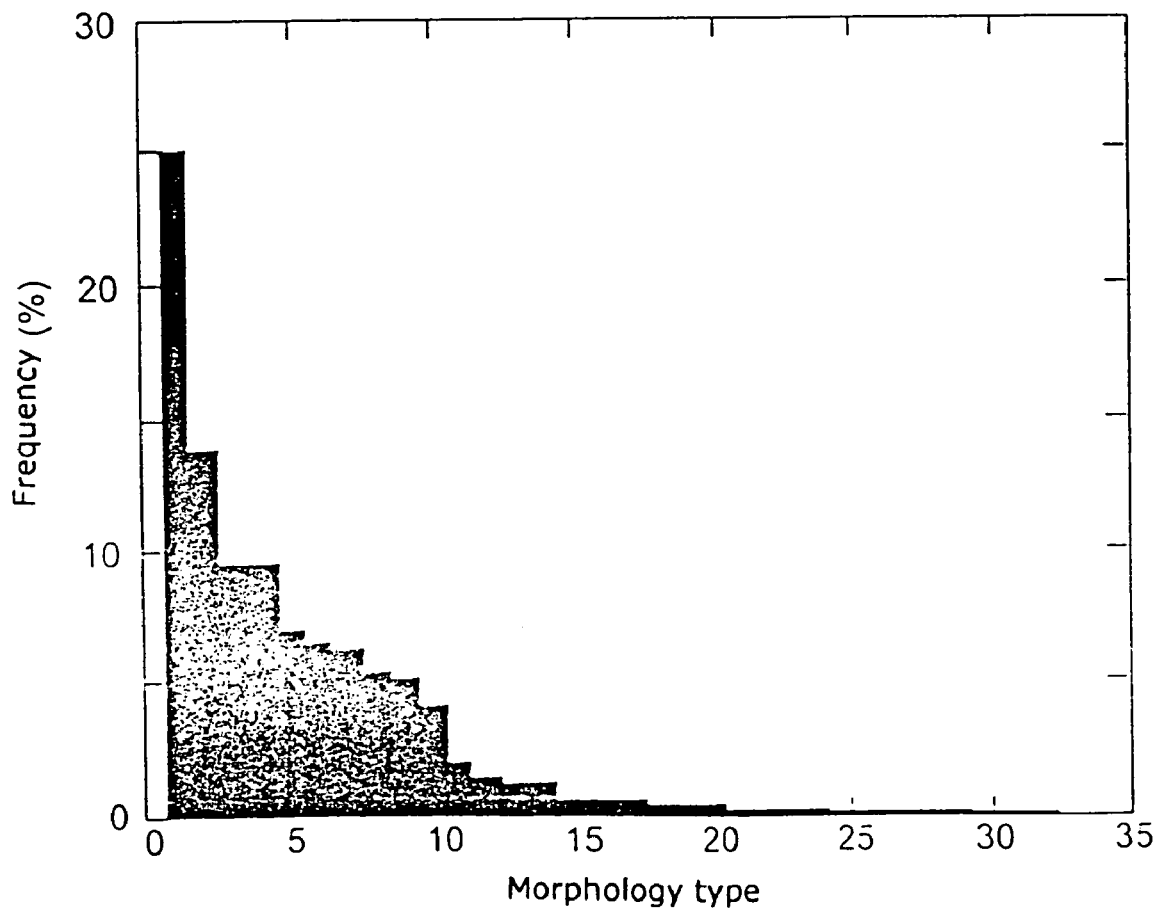
Fig.2   Distribution of IEGM morphologies $X = K1(w(WW) * X\_P) + K0$    K0,K1: Context-dependent correction functions $Y = Y\_P * (-1)^S * (AAAA)$    Default: K0 = 0 ms, V-pace: K0 = 40 ms $X\_P = [xp(1), ........ xp(n)]$    w(WW): Mapping onto the centers of the width classes $Y\_P = [yp(1), ........ yp(n)]$

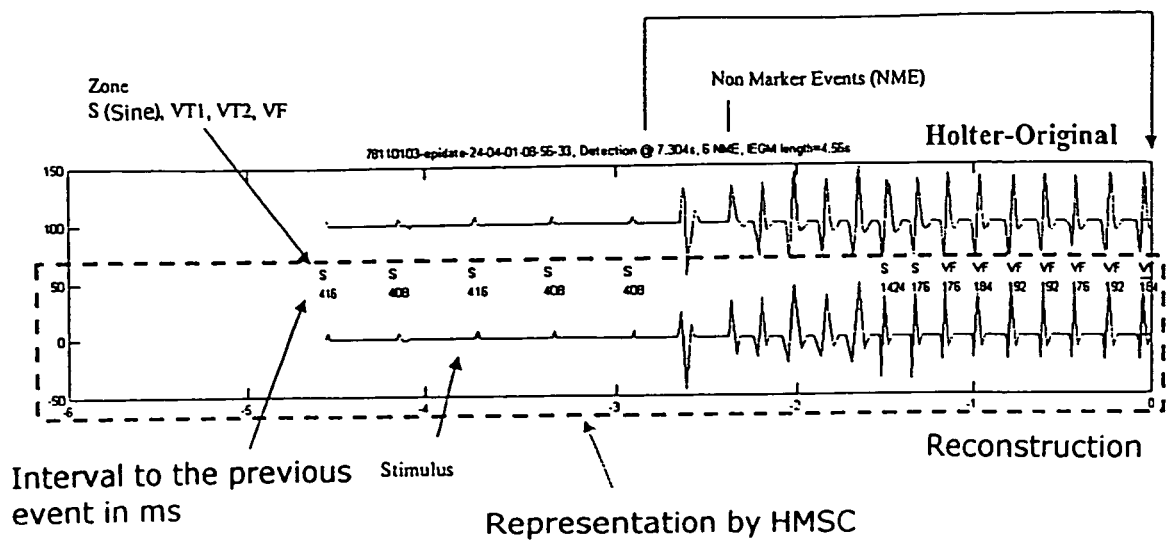
Figure 10: Original and reconstruction an IEGM signal

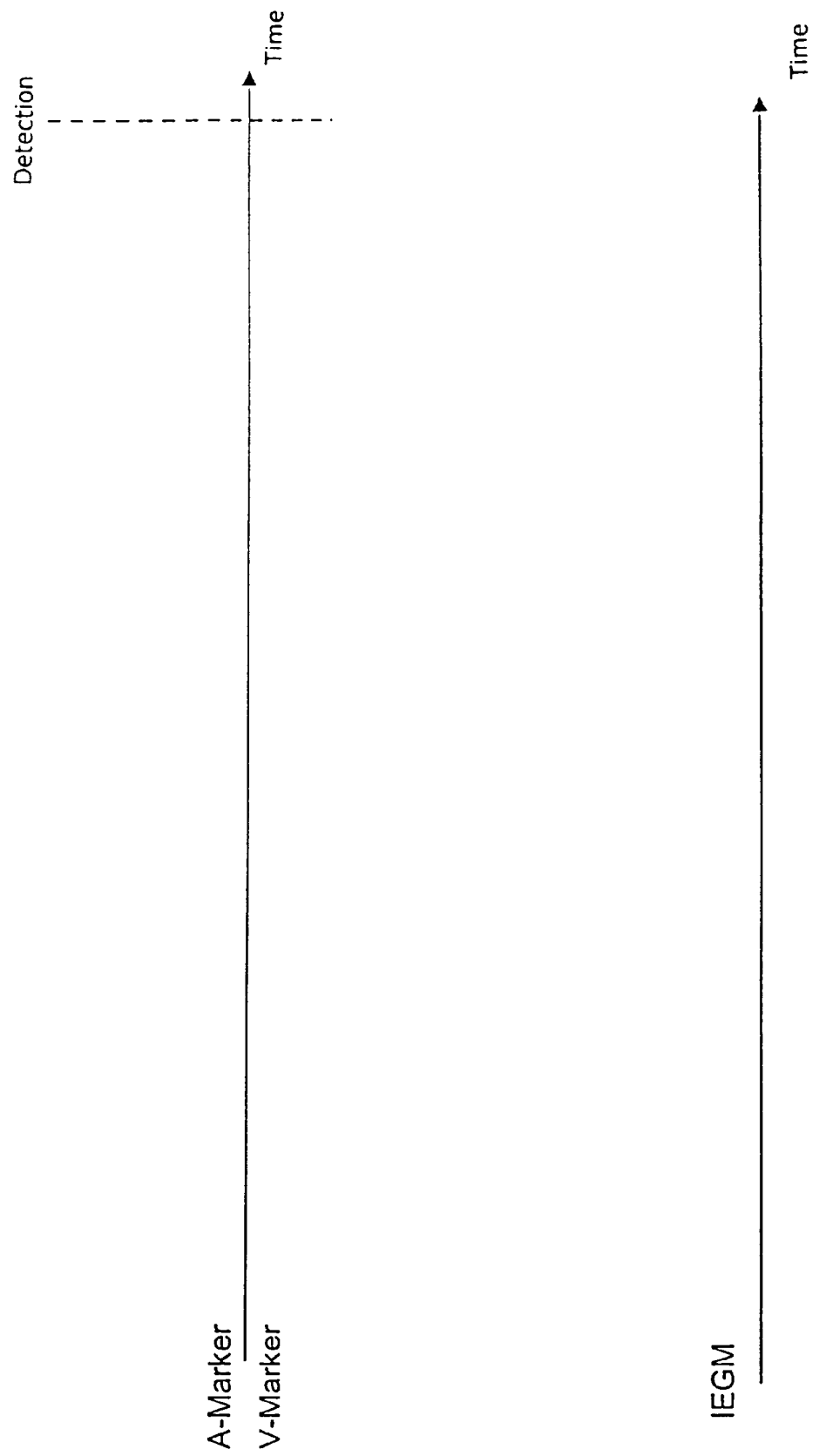
Figure 11a : IEGMString:

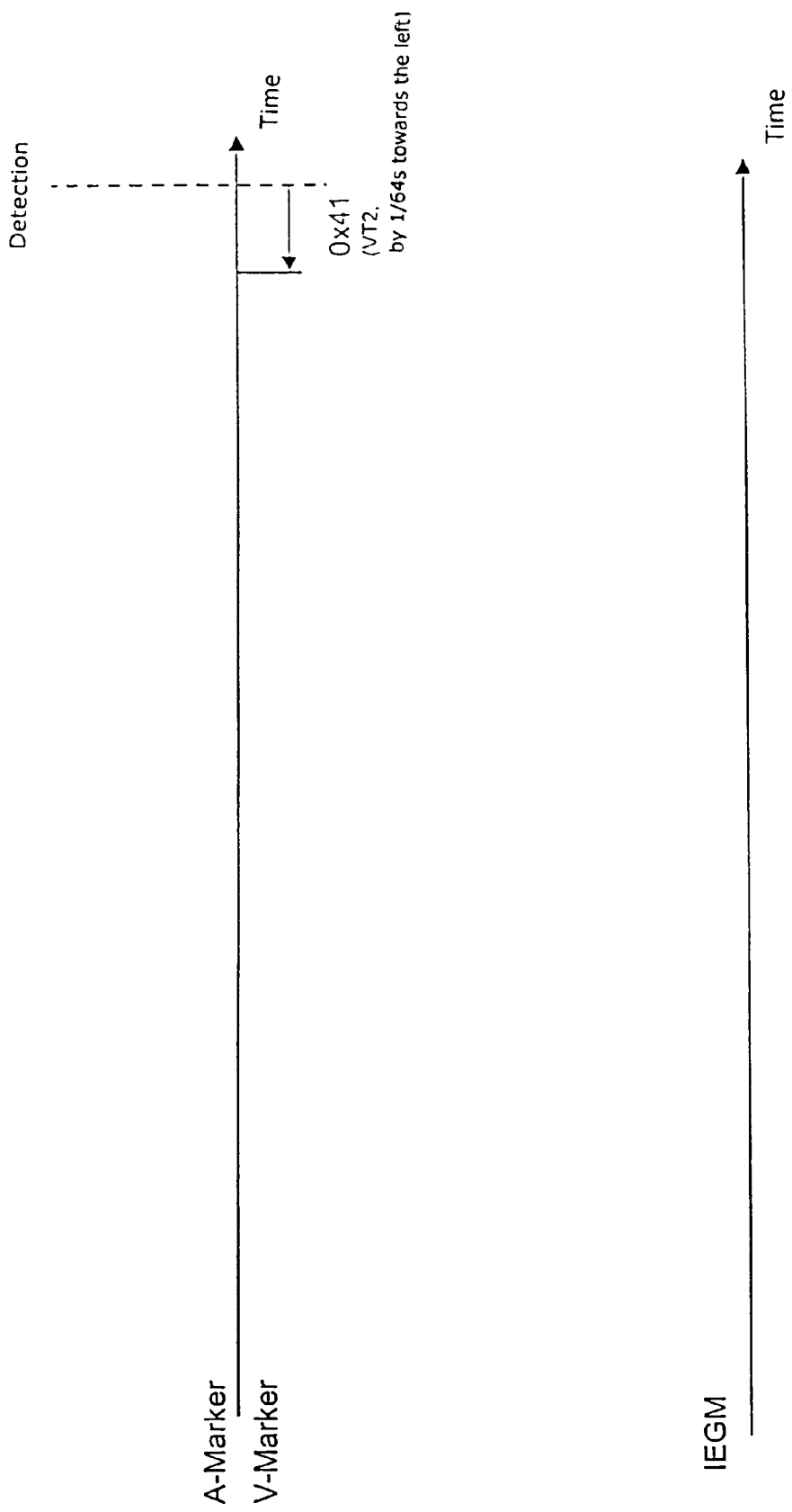
Figure 11b : IEGMString: 41

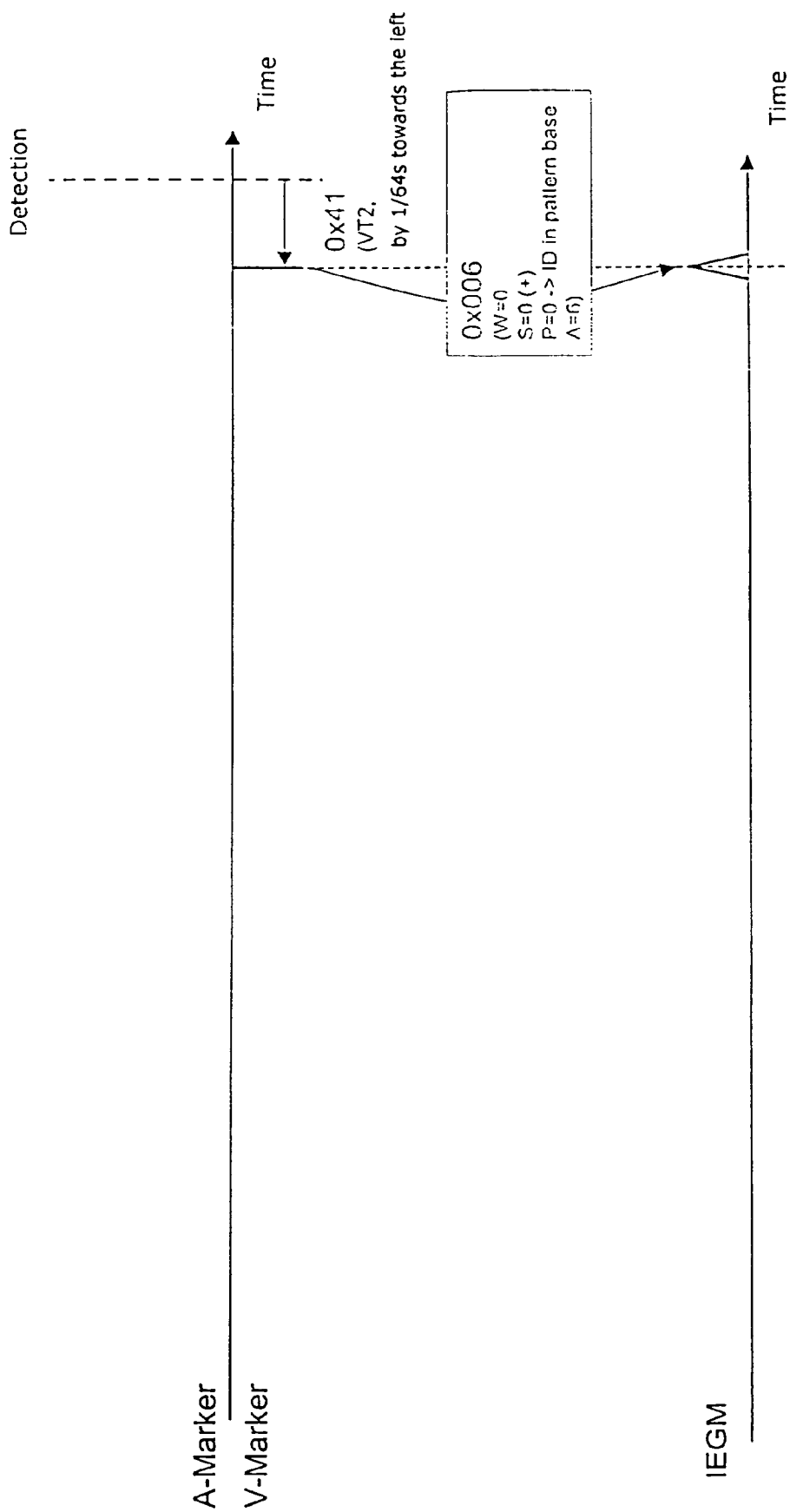
Figure 11c: IEGMString: 41006

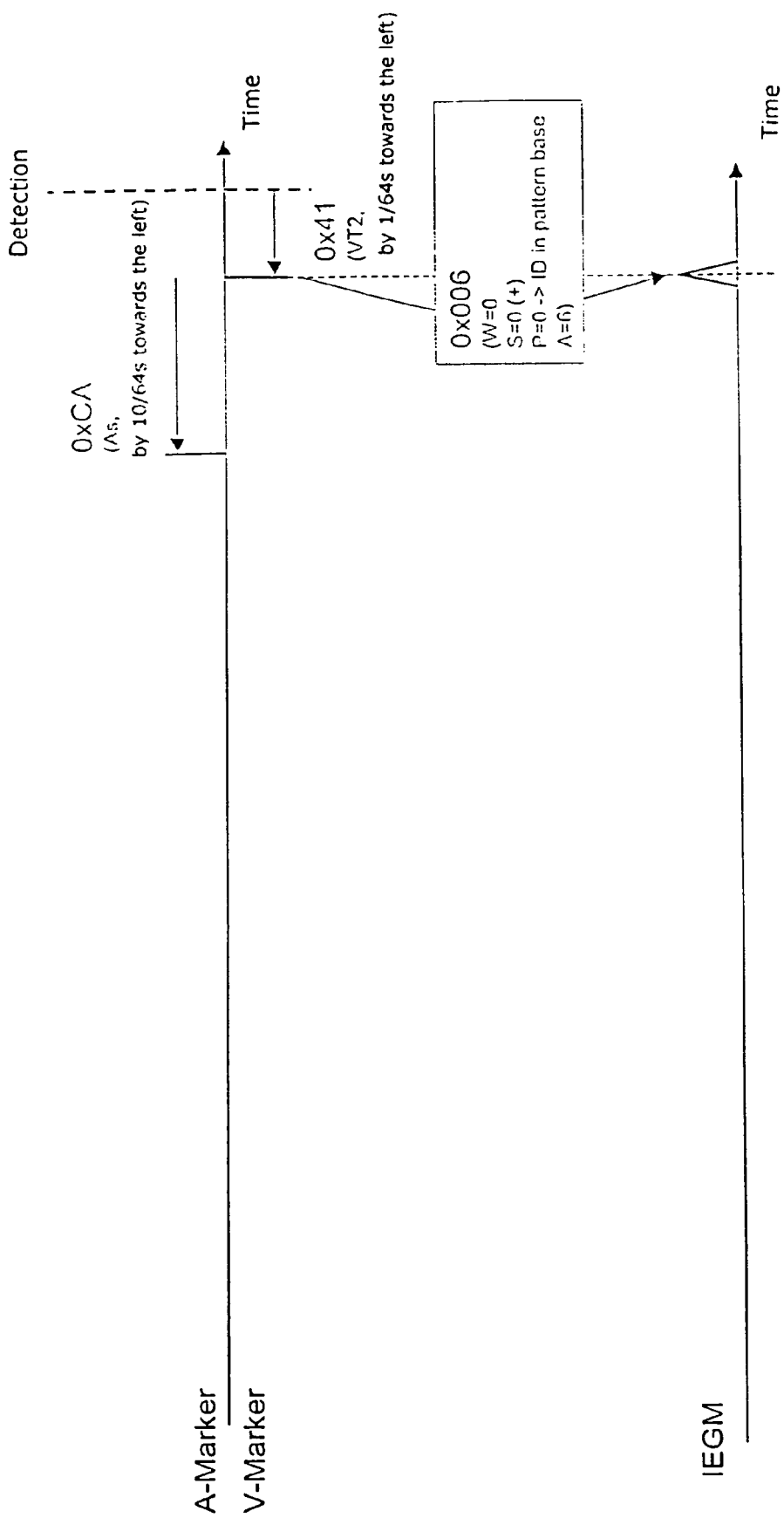
Figure 11d : IEGMString: 41006CA

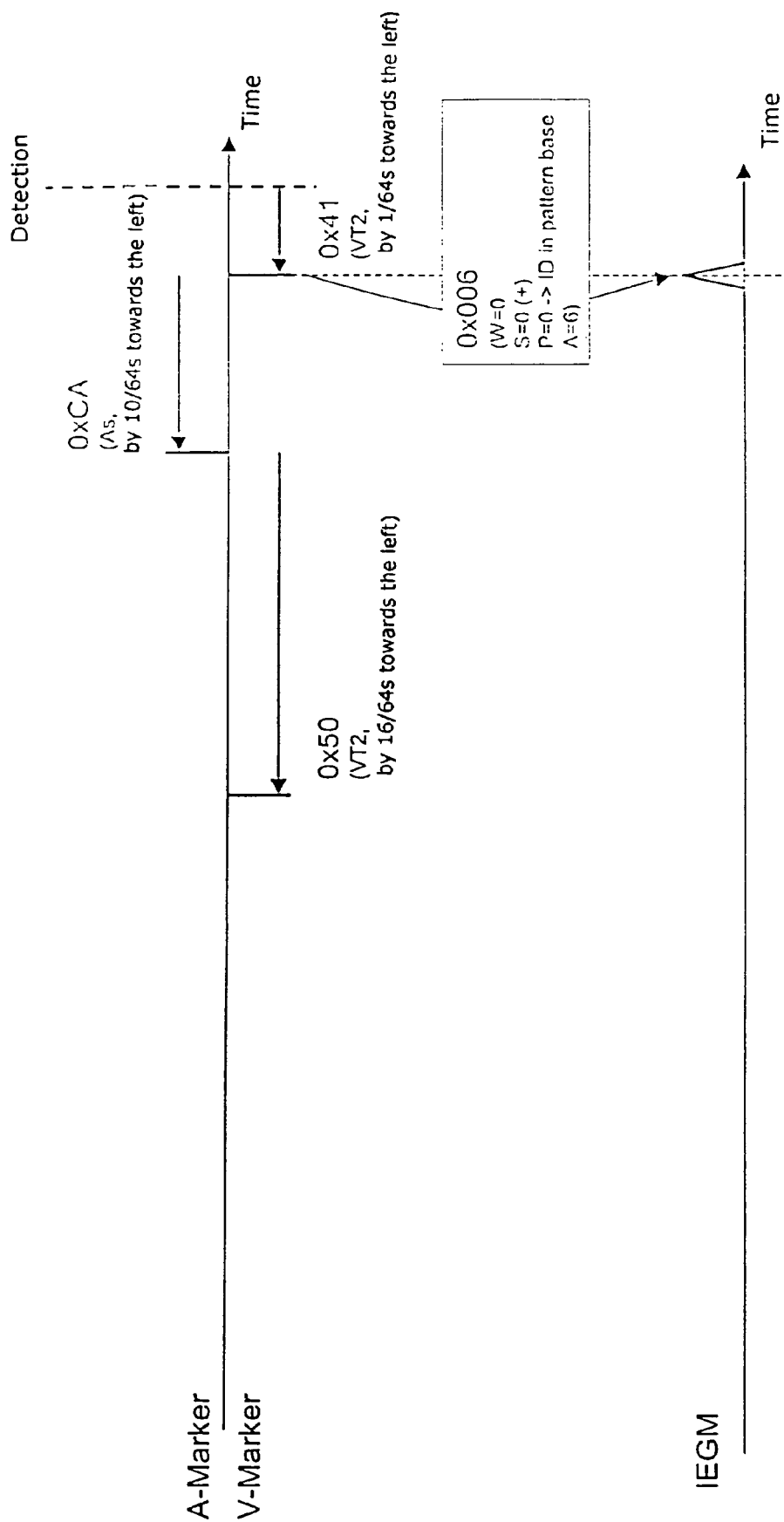
Figure 11e :  IEGMString: 41006CA50

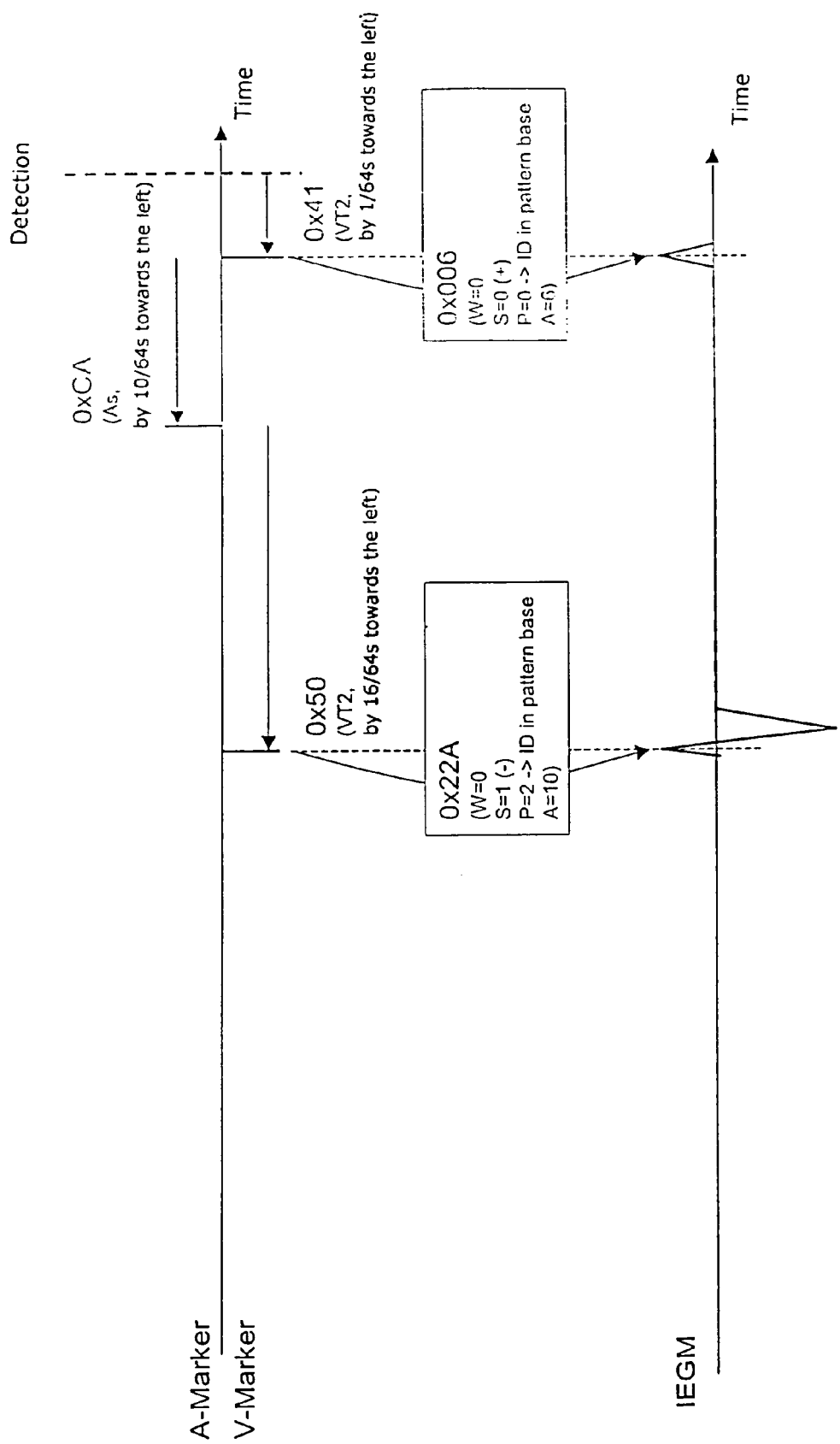
Figure 11f : IEGMString: 41006CA5022A

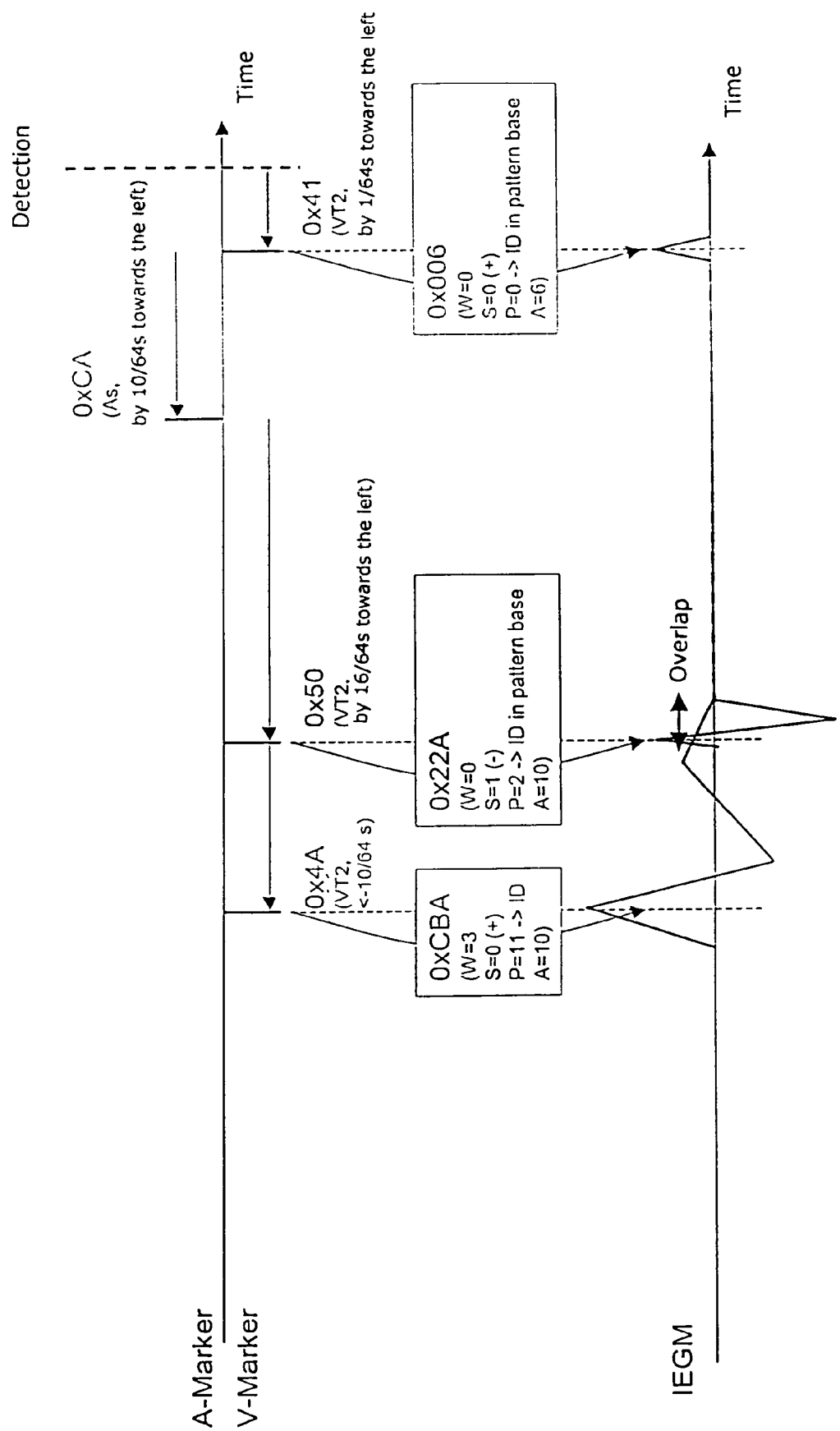
Figure 11g : IEGMString: 41006CA5022A4ACBA

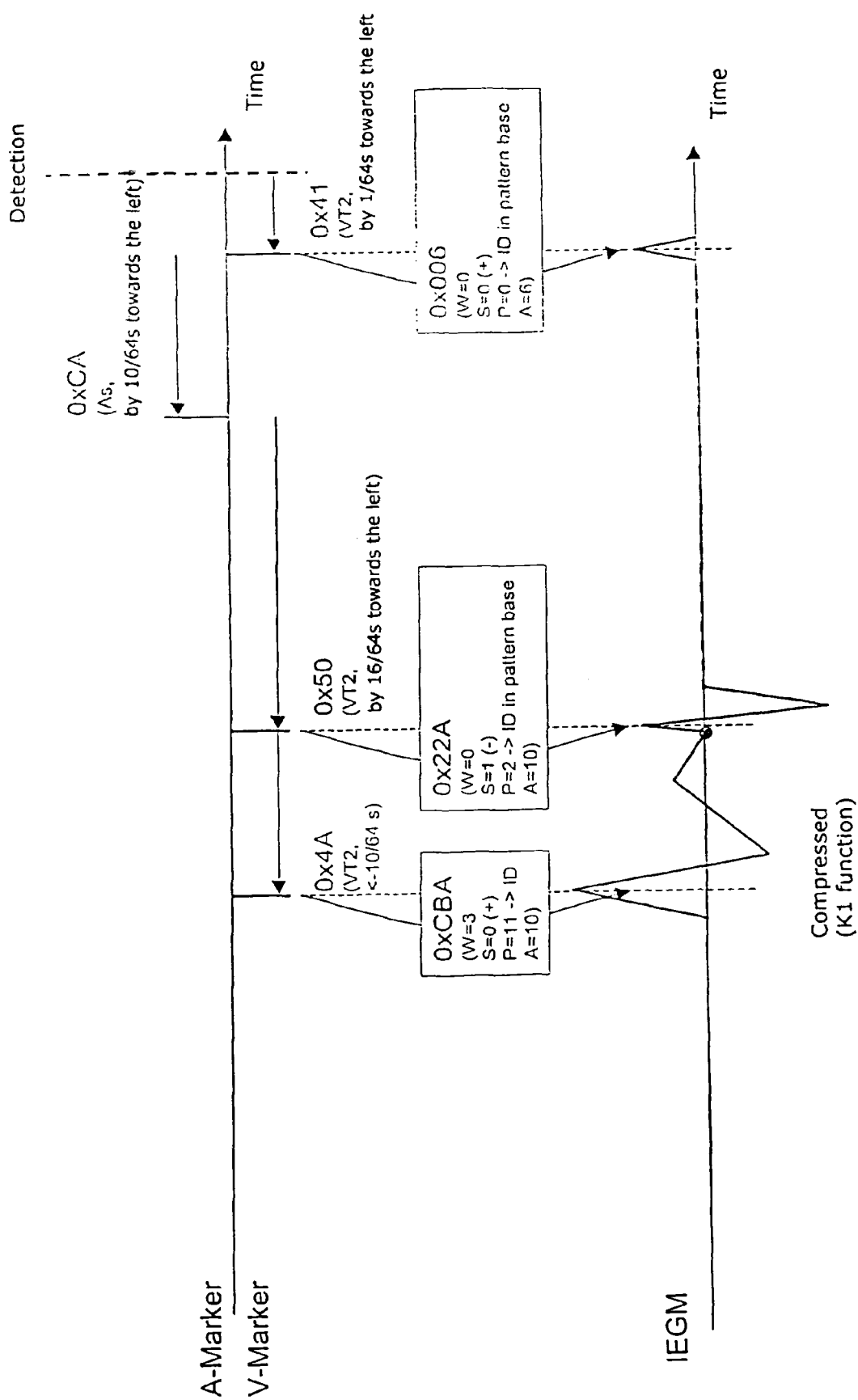
Figure 11h :  IEGMString: 41006CA5022A4ACBA

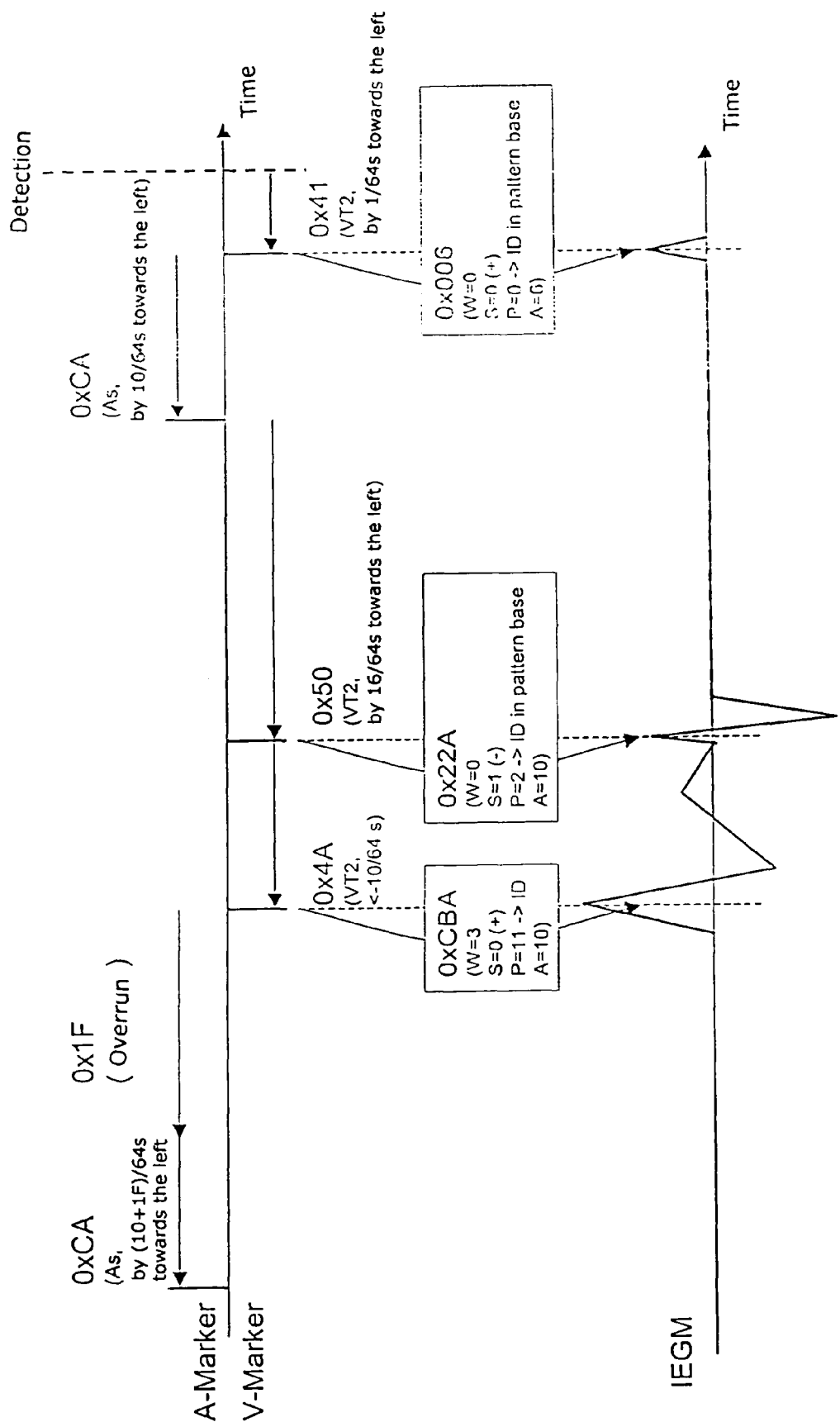
Figure 11i :  IEGMString: 41006CA5022A4ACBA1FCA

SIGNAL PROCESSING APPARATUS FOR PHYSIOLOGICAL SIGNALS

CROSS-REFERENCE TO RELATED APPLICATIONS/INCORPORATION BY REFERENCE

This U.S. patent application claims priority to German patent application 10 2004 043 005.5 filed Sep. 2, 2004.

TECHNICAL FIELD

Certain embodiments of the present invention relate to a signal processing apparatus for processing physiological signals and an implantable medical device. More particularly, certain embodiments of the present invention relate to a cardiac pacemaker having such a signal processing apparatus.

BACKGROUND OF THE INVENTION

A particular situation of use is the transmission of an intracardiac electrocardiogram which is recorded for example by means of a cardiac pacemaker or an implantable cardioverter/defibrillator (ICD) and which is to be transmitted to the exterior from the implant for expert assessment by a physician or for processing by an external device. Preparation of the intracardially measured electrocardiogram and the wireless transmission thereof to an external device require energy which is only limitedly available in the implant. A high level of energy consumption would entail a short service life for the implant and would oblige the person bearing such an implant to undergo an unnecessarily large number of operations for replacement of the implant.

Further limitations and disadvantages of conventional, traditional, and proposed approaches will become apparent to one of skill in the art, through comparison of such systems and methods with the present invention as set forth in the remainder of the present application with reference to the drawings.

SUMMARY OF THE INVENTION

Embodiments of the present invention quite generally concern the problem of processing physiological signals in a manner such that the physiological signals can be transmitted at the lowest possible complication and expenditure, in particular in terms of a low energy consumption.

With the background in mind, various embodiments of the present invention afford signal preparation of a physiological signal, which is itself resource-sparing and which allows the transmission of such a signal with little data.

In accordance with various embodiments of the present invention, such a resource-sparing device is attained by a signal processing apparatus of the kind set forth in the opening part of this specification, which has an input stage for the preparation of a physiological signal, in particular an electrocardiogram, which is adapted to provide a signal of an alternating polarity, which is formed from the physiological signal and which is to be evaluated, and is connected to an evaluation stage for forwarding of the signal to be evaluated. The evaluation stage is adapted to respond to a reference moment in time associated with the physiological signal and, for a signal segment, associated in respect of time with the reference moment in time, of the signal to be evaluated, to detect a respective amplitude value for at least some characteristic curve points contained in the signal segment (for example signal maxima and minima, inflection points and so forth) and to generate from the amplitude values obtained in that way a morphology code which describes the form, that is to say the visual appearance, of the respective signal segment so that the visual appearance of the signal segment can be sufficiently accurately reconstructed by means of the morphology code.

Embodiments of the present invention are based on the realization that a visual reproduction of a physiological signal, which is sufficiently informative for example for a physician, is already to be reconstructed when, for a respective signal segment, the amplitudes of the signal maxima and minima as well as the time position thereof in relation to a reference moment in time are detected. Accordingly, embodiments of the present invention provide a signal processing apparatus with an evaluation stage which is responsive to a reference moment in time and which, for a signal segment associated with the reference moment in time, detects the characteristic curve points, that is to say at least the signal minima and maxima and the amplitude values thereof, and generates a morphology code from those values. The step of determining the signal minima and maxima and more specifically, in accordance with an embodiment of the present invention, the absolute signal minima and maxima between each two respective zero crossings of the signal distinguishes the signal processing apparatus according to an embodiment of the present invention from other known signal processing apparatuses in which, for example, an electrocardiogram is sampled at short regular time intervals and the signal obtained in that way is subjected to further processing with conventional, data-reducing methods such as, for example, ZIP compression which is known from office data processing in order to reduce the amount of the data to be transmitted. The morphology code to be produced with the signal processing apparatus, in accordance with an embodiment of the present invention, also serves to reduce the amount of data to be transmitted. That is achieved in that only the data of a physiological signal, which is decisive in terms of visual representation, determine the morphology code and are represented thereby.

The reference moment in time to which the evaluation stage responds is, in accordance with an embodiment of the present invention, a moment in time at which a physiological event, for example, a ventricular contraction, is reflected in the physiological signal, which in the case given by way of example occurs in the form of an R spike. Accordingly, the signal processing apparatus is adapted to process electrocardiograms as physiological signals and to respond to a respective R spike in the electrocardiogram as the reference moment in time. In relation to signal segmentation, this means that a respective signal segment which is worked by the evaluation stage is associated precisely with one cardiac cycle.

In accordance with a variant embodiment of the signal processing apparatus, the output stage has at least one zero crossing detector which is adapted to detect zero crossings of the signal to be evaluated, within a signal segment. The zero crossing detector can be a zero line crossing detector and, in accordance with an embodiment of the present invention, is a zero band crossing detector, for example, a Schmidt trigger. While a zero line crossing detector uses the same reference value (zero value) for a zero crossing from positive to negative and vice-versa, that reference value for the transition from positive to negative is lower than for the transition from negative to positive so that this gives a zero band which is determined by the two different reference values and which affords a hysteresis effect.

In addition, in accordance with an embodiment of the present invention, the signal processing apparatus has a minimum/maximum detector which is adapted to detect a respective absolute signal minimum or maximum of the signal to be evaluated, between two respective adjacent zero crossings, in respect of the amplitude thereof and also the relative position on a time axis with respect to a reference signal. The reference signal is, for example, an R spike whose moment of occurrence forms the reference moment in time and whose amplitude forms a reference value for detection of the amplitudes of the signal maxima and minima in the same signal segment. The evaluation signal produced by the evaluation unit should also reflect a scaling factor which, for example, reproduces the reference signal amplitude and thus the factor with which the relative amplitudes of the signal maxima and minima are to be scaled. The evaluation signal obtained in that way at least partially also determines the morphology code to be obtained.

This would already indicate that the evaluation unit is, in accordance with an embodiment of the present invention, adapted to segment-wise evaluate the signal to be evaluated, which was obtained from the physiological signal by way of the input stage. That is effected in such a way that a respective signal segment includes a period of time beginning prior to the reference moment in time and terminating after the reference moment in time. The period of time is established in such a way that it is shorter than the period between two successive reference moments in time so that adjacent signal segments do not overlap, in accordance with an embodiment of the present invention.

In regard to the last-mentioned aspect, it is advantageous if the input stage or the evaluation stage are so adapted to segment the physiological signal in such a way that a respective signal segment includes a signal associated with a recurring physiological event, in particular the reference signal in the above-indicated sense. The evaluation stage is then adapted to generate, for each signal segment, a respective morphology code, in dependence on the evaluation signal for the respective signal segment. As already indicated, for that purpose, the signal to be associated with the recurring physiological event serves as the reference signal, in accordance with an embodiment of the present invention. The reference signal is, for example, a respective R spike if the physiological signal and the evaluation signal is an ECG. The reference signal amplitude is, in accordance with an embodiment of the present invention, the absolute maximum or the absolute minimum of the signal to be evaluated within the respective signal segment and thus, at the same time, the amplitude value of the reference signal. Accordingly, the reference signal time is the moment in time, which is to be associated with the reference signal as the recurring physiological signal, of the occurrence in the respective signal segment. The reference value both for an analysis of the (relative) amplitudes of the signal maxima and minima within a signal segment and also for the moment in time of the occurrence thereof is thus, in accordance with an embodiment of the present invention, a reference signal which at the same time corresponds to the absolute maximum or absolute minimum of the signal to be evaluated within a signal segment. That makes it possible to transmit, as the scaling factor only, one single value which reflects the reference signal amplitude and otherwise to describe the secondary maxima and minima of the signal to be evaluated within the signal segment by relative amplitude values which are related to the reference signal amplitude. At the same time, the reference signal moment in time is, in accordance with an embodiment of the present invention, the reference moment in time in the above-indicated sense.

In order to obtain the reference moment in time, the evaluation unit, in accordance with an embodiment of the present invention, can be connected to a marker signal generator which is adapted to evaluate a physiological signal and to generate a marker signal which characterizes an event to be associated with the physiological signal, for example, a cardial event such as an R spike or a ventricular contraction, in which respect the evaluation unit is adapted to respond to the moment in time given by a marker signal, as the respective reference moment in time. In that way, the reference moment in time would not be formed intrinsically from the signal to be evaluated, but extrinsically by the marker signal unit which equally processes a signal obtained from the physiological signal, as an input signal.

In accordance with an embodiment of the signal processing apparatus, the evaluation unit thereof is adapted, for the purposes of forming the morphology code, to classify the relative amplitudes of the signal maxima and minima in a few amplitude classes in dependence on the relative magnitude of the signal maxima and minima in relation to the reference signal amplitude. The evaluation unit then forms the morphology code in such a way that the morphology code includes a pattern subcode which can assume a few values and reflects the association of the respective amplitude of a signal maximum and minimum with one of the amplitude classes. For association of the amplitudes of the signal maxima and minima with a respective amplitude class, the evaluation stage is adapted to determine whether the respective amplitude of a signal maximum or minimum, in relation to the reference signal, is similarly large—that is to say just as large or only slightly smaller—, medium—large or small. That association is advantageous in particular when the reference signal amplitude is the largest signal amplitude of the signal to be evaluated within a signal segment. An association with one of a total of four amplitude classes "0", "small", "medium" and "large" can be effected, for example, in such a way that each signal minimum or maximum with an amplitude value whose magnitude is between 75 and 100% of the reference signal amplitude value is associated with the amplitude class "large". Correspondingly, a relative amplitude value of a signal minimum or maximum is associated with the amplitude class "medium" if the amplitude value thereof is between 37.5 and 75% of the reference signal amplitude value. The amplitude class "small" is associated with a signal maximum or minimum whose relative amplitude value is between 12.5 and 37.5% of the value of the reference signal amplitude. The amplitude class "0" is associated with a signal maximum or minimum whose relative amplitude value is between 0 and 12.5% of the reference signal amplitude value.

The information, obtained in this way, about the relative amplitudes of the signal maxima and minima respectively is, in accordance with an embodiment of the present invention, processed by the evaluation stage in such a way that the evaluation stage reproduces those relative amplitude values by an event code which, for each signal maximum and minimum, contains an amplitude digit ($\alpha$) which can assume one of a few, for example, four values (the four values corresponding to the number of the amplitude class, for example "0", "small", "medium" and "large") and which uniquely describes the association of the respective signal maximum or minimum with one of the amplitude classes. In the generalized case of a curve point detector, the ascertained digit is a characteristic digit ($\alpha$).

For that purpose the evaluation stage is, in accordance with an embodiment of the present invention, adapted to form the event code in such a way that it contains a few, for example, four amplitude digits which respectively reflect the amplitude of a total of four signal maxima or minima, which are adjacent to the reference signal, within the respective signal segment.

The four signal maxima or minima can in that case occur at both sides of the reference signal (left and/or right).

In that way, solely the event code already forms a data-reduced representation of a respective signal segment. A further data reduction can be achieved if the evaluation stage is adapted to form a pattern subcode (PPPPP) from the event code, by one or more event codes being associated with a pattern subcode value by way of a look-up table. Data reduction occurs when a plurality of event codes are respectively associated with a pattern subcode. It has been found that 32 pattern subcodes are sufficient to be able to sufficiently precisely describe all signal segments of an ECG, which occur in practice, as the signal to be evaluated.

Besides a description, obtained from the event code, of a respective signal segment in relation to the relative amplitudes of the signal maxima and minima, the pattern subcode, in accordance with an embodiment of the present invention, includes a sign digit (S, also referred to hereinafter as the signum) which reflects the sign of the reference signal amplitude, that is to say whether the reference signal amplitude is positive or negative.

In addition, the morphology code, in accordance with an embodiment of the present invention, includes a signal width subcode (WW) which, for example, represents the time distance between a first signal maximum or minimum and the last signal maximum or minimum within a signal segment or alternatively also the duration of a signal segment.

In order to represent the scaling factor, the morphology code, in accordance with an embodiment of the present invention, includes a scaling subcode (AAAA) which forms the scaling factor and which reflects the reference signal amplitude as an absolute value.

The morphology code is, in accordance with an embodiment of the present invention, a binary code which has one or more of the following constituents (subcodes):

a signal width subcode (WW) which, in accordance with an embodiment of the present invention, includes at least two binary digits, a sign subcode (S) which, in accordance with an embodiment of the present invention, includes one binary digit, a pattern subcode (PPPPP) which, in accordance with an embodiment of the present invention, includes at least five binary digits, and a scaling subcode (AAAA) which, in accordance with an embodiment of the present invention, includes at least four binary digits.

In addition, the evaluation unit is, in accordance with an embodiment of the present invention, adapted to associate a time code with the morphology code and suitably add same.

For signal preparation purposes. the input stage, in accordance with an embodiment of the present invention, includes a band pass filter which is adapted to generate, from the physiological signal, a signal which is to be evaluated and which is differentiated and has accordingly zero crossings.

The signal processing apparatus is, in accordance with an embodiment of the present invention, a component part of an implantable electromedical device which also has a telemetry unit which, at the input side, is connected to the signal processing apparatus and serves to wirelessly transmit the morphology code to an external device.

The physiological signal can then be reconstructed in the external device on the basis of the morphology code in respect of the form thereof.

The foregoing description involved the use of a conceptuality in accordance with which the physiological signal is the input signal of the input stage, for example, an intracardiac electrocardiogram (iEGM). The output signal of the input stage and thus the input signal of the evaluation unit is the signal which is to be evaluated and which was obtained by the input stage from the physiological signal. The evaluation stage includes a minimum/maximum detector whose output signal is the evaluation signal (not to be confused with the signal to be evaluated) which reflects the signal maxima or minima of the signal to be evaluated, within the signal segment.

The reference moment in time selected for evaluation of the signal segments can be an extrinsically obtained moment in time, for example the moment predetermined by a marker signal, or an intrinsically obtained moment in time which is derived from the signal to be evaluated, for example, the moment of the occurrence of the greatest signal value within the signal segment to be evaluated. The greatest signal value is also treated as a reference signal whose amplitude value is identified as the reference signal amplitude and whose moment of occurrence is the reference signal moment and can serve as an intrinsically obtained reference moment in time.

A signal segment is a portion of the signal to be evaluated and is associated with a respective moment in time. A signal segment includes a respective period of time which extends from the beginning to the end of a signal segment.

The reference signal as well as further signal maxima or minima are also referred to hereinafter as spikes. A central signal spike, in accordance with an embodiment of the present invention, forms the reference signal. The secondary maxima and minima within a signal segment form satellite spikes.

These and other advantages and novel features of the present invention, as well as details of illustrated embodiments thereof, will be more fully understood from the following description and drawings.

BRIEF DESCRIPTION OF SEVERAL VIEWS OF THE DRAWINGS

FIG. 1 illustrates the establishment of significant signal spikes, in accordance with an embodiment of the present invention;

FIG. 2 shows an overview of a typical frequency distribution of morphologies of intracardiac electrocardiograms, in accordance with an embodiment of the present invention;

FIG. 10 shows an example of an original of an electrocardiogram and the corresponding reconstruct after evaluation of the morphology code, in accordance with an embodiment of the present invention; and FIGS. 11a through 11i show the reconstruction of the configuration of the encoded physiological signal, in accordance with an embodiment of the present invention.

DETAILED DESCRIPTION OF THE INVENTION

Figure 3:
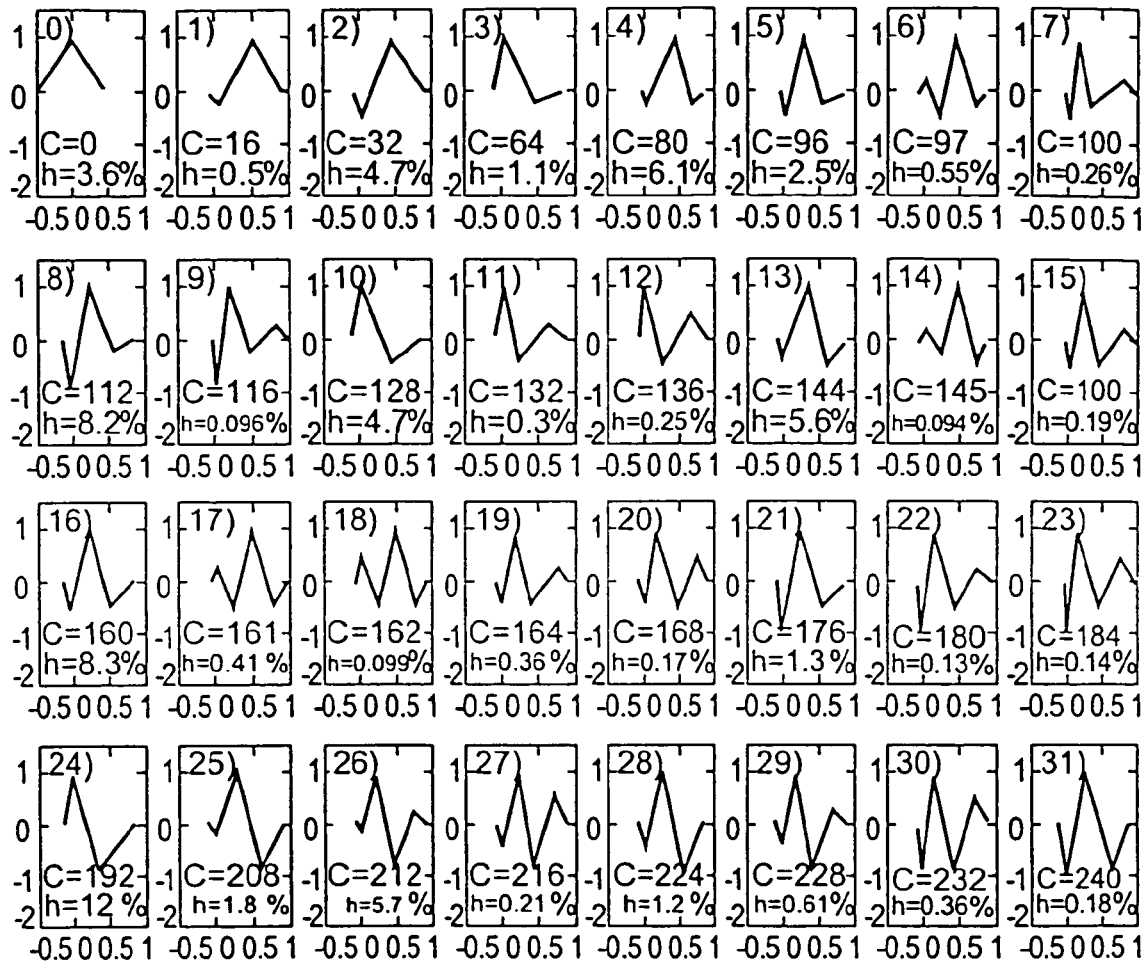
FIG. 3 reflects 32 typical patterns of signal segments of an iEGM, which are sufficient to sufficiently accurately describe an iEGM, in accordance with an embodiment of the present invention.

The signal processing apparatus set forth herein implements a method which makes it possible to encode and decode parameter sets which are obtained from a signal to be evaluated and which describe the functional state of the heart in a time window (signal segment of the signal to be evaluated) around a given reference moment in time (event-triggered or planned) in very compact form.

The mode of operation of the signal processing apparatus is based on the extraction of characteristic features from event-discrete cardiac measurement signals which are to be used for a diagnostic analysis and/or therapy control. The definition of the morphological features and the encoding thereof are based in that respect on the principles of visual perception. A basic idea of the method is to be able to approximate the signal morphologies which occur by a finite (possibly greatly reduced) set of representative signal patterns, upon reconstruction. The method can be applied to time-limited signal portions (event sequence) but it is also online-capable and is suitable for continuous encoding of individual events.

Typical physiological signals, in particular cardiac measurement signals, for which the method can be used, are:

derivations of intracardiac electrograms (for example tip-rig iEGM, MAP, VER, farfield iEGM)

intracardiac/intrathoracal impedance signals blood pressure signals and so forth.

The signal sources can be single-channel or multi-channel. In the expanded sense the method can be applied to any event-discrete signals (for example respiration (minute ventilation), given EEG waves and nerve signals, rhythmic glandular functions, swallow reflex, blinking and so forth).

Possible uses of the method for event-discrete signals are:

Optimized storage (data compression with a memory requirement of preferably less than 2.5 bytes/event with a maximum spacing of 64 sample intervals between 2 events);

Optimized transmission (reduced data rate for narrow-band transmission channels, for example home monitoring or other applications in telemedicine);

Semantic data structuring (as preparatory processing for computer-aided evaluation such as automated context-related diagnosis in a home monitoring center);

Part of the feedback branch of a therapeutic regulator (closed-loop therapy: for example in respect of frequency matching; automatic capture control, automatic AA-, AV-, VV-delay, mode-switch control);

Farfield suppression and rhythm discrimination (for example in ICDs SVT/VT) based on items of morphological information (context analysis over phases from morphological descriptors);

Boundary conditions/requirement for applicability;

Compact signal description is achieved by the utilization of the following boundary conditions which are ensured by an input stage (see FIG. 4) of the signal processing apparatus:

Nature of the signal to be evaluated:

The method presupposes that the significant morphological information derives from the extremes of the signal configuration, which are respectively determined between each two zero band crossings. In that respect, it is assumed for a respective signal segment to be analyzed that it starts from a zero line and also ends again at the zero line. If a plurality of local extremes are to be found between the adjoining zero band crossings, only the absolute extreme in the respective range is deemed to be relevant; the other peaks are disregarded. The consequence of this is that the sequence of the relevant extremes determined in that way is distinguished in that the polarity thereof is always alternating. That information (alternation of the polarity) is therefore redundant and does not have to be transmitted (FIG. 1).

The method further presupposes that each one of the signal segments being considered can be sufficiently well approximated by a corresponding representative from a finite number of different characteristic morphologies (event patterns). A typical frequency distribution for morphologies in respect of right-ventricular tip-ring IEGMs and typical patterns is shown in FIGS. 2 and 3. Accordingly 32 patterns are sufficient for encoding IEGM signals with this method.

Figure 4:
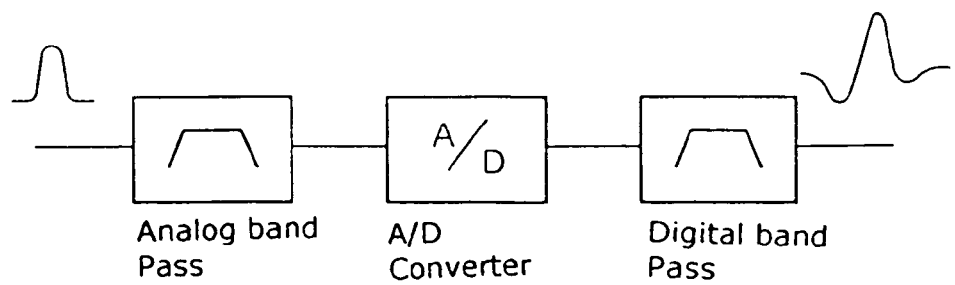
FIG. 4 shows a block circuit diagram of a transmission channel by way of example as an input stage for the signal processing apparatus, in accordance with an embodiment of the present invention.

Signal conditioning in the input stage:

The input stage shown by way of example in FIG. 4 generates, from the respective physiological signal, for example an intracardially derived signal, a signal to be evaluated, which is suitable for further evaluation by an evaluation stage.

Intracardially derived signals which are recorded by an implant are always subjected to band-pass filtering. The high pass component results from the capacitive coupling of the device to the tissue in order to avoid a damaging DC current flow. The low pass serves as an antialiasing filter for subsequent sampling (see FIG. 4, analog band pass). As preliminary processing for the sensing stage of a cardiotherapeutic implant, the digitized signal is subjected to further band pass filtering (see FIG. 4, digital band pass), whose greatly differentiating effect on the signal typically results in a desired signal configuration with peaks which alternate in respect of polarity. The demands on the nature of the signal source are satisfied to a very good level of approximation, for the signals which are pre-processed in that way.

If that is not the case however that method can be artificially preceded by suitable signal conditioning which is to be compensated again after reconstruction. That is admittedly only approximately possible but it is adequate for most practical requirements. An improvement in the results involved can be achieved by the transmission of additional signal metrics (for example signal area).

Figure 6:
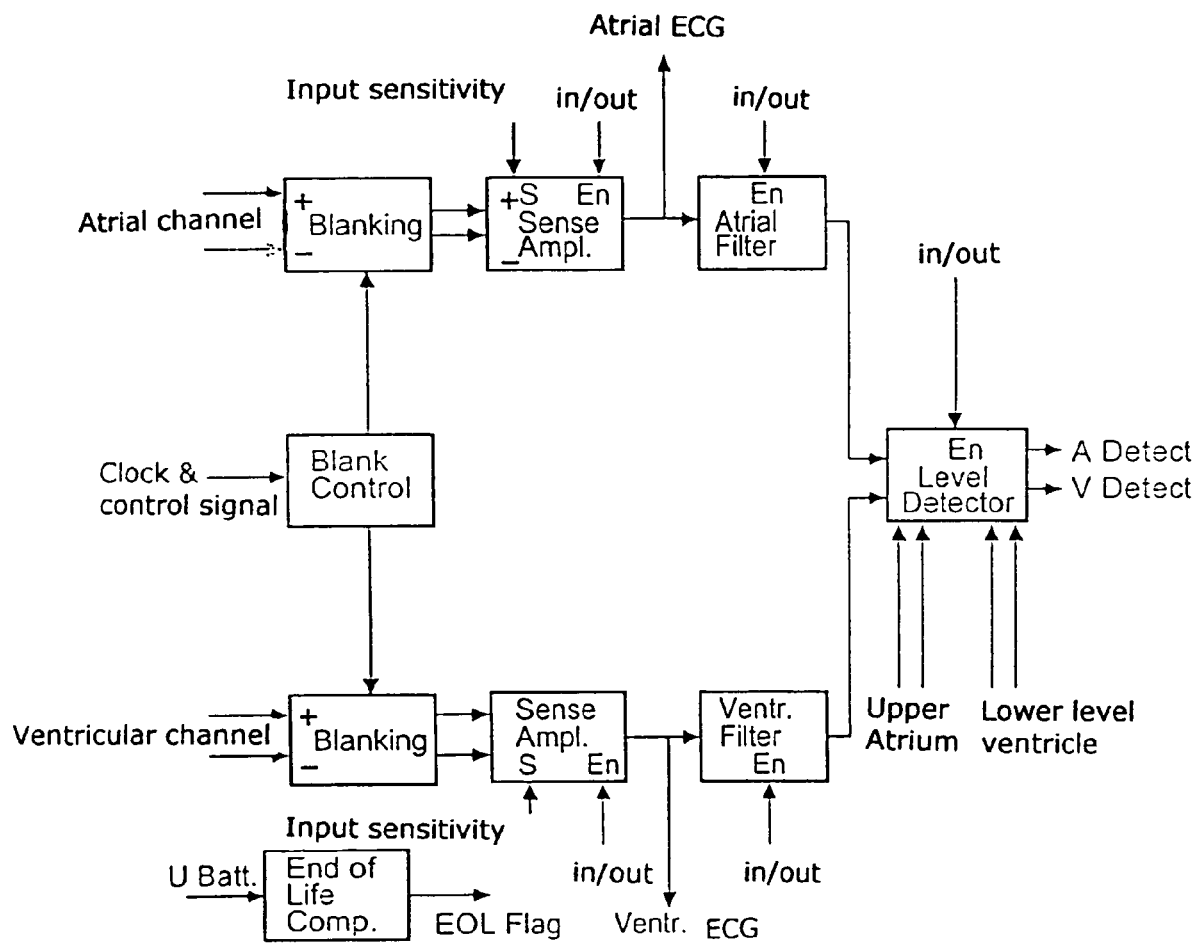
FIG. 6 shows a block circuit diagram of a typical marker signal generator, in accordance with an embodiment of the present invention.

Use of items of information which are already available in the implant:

A cardiotherapeutic implant derives its therapy decision from items of information about the instantaneously occurring cardiac activity so that segmentation of the signal is thus already involved. The segments are characterized by so-called "markers" generated by a per se known marker signal generator as is shown in FIG. 6. Such a marker signal occurs at the outputs of the level detector in FIG. 6, which are identified by "V-sense" and "A-sense", as soon as a ventricular or an atrial event has been detected.

Figure 5:
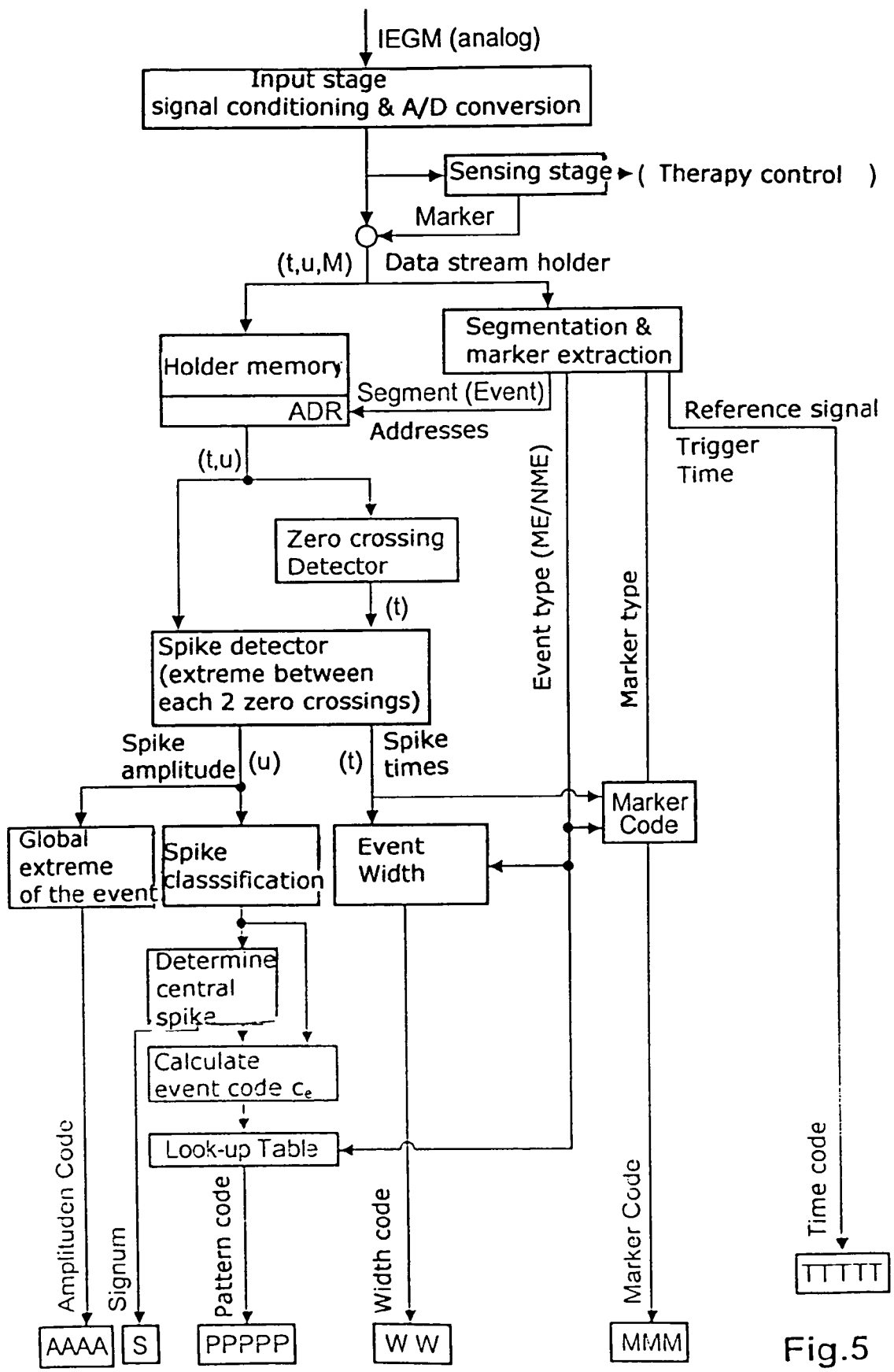
FIG. 5 shows a block circuit diagram of an evaluation stage by way of example for the signal processing apparatus, in accordance with an embodiment of the present invention.
Figure 7:
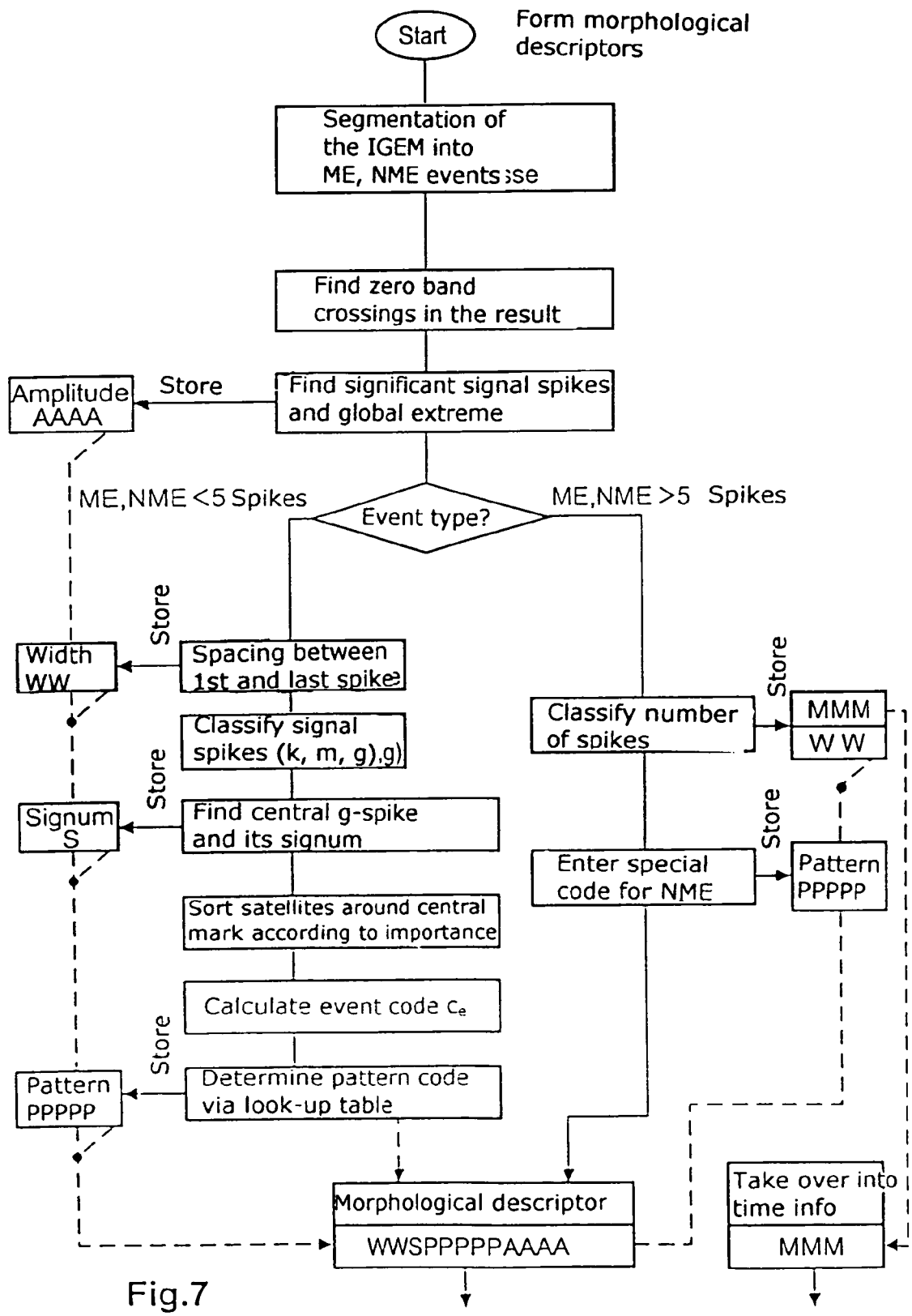
FIG. 7 shows a signal flowchart representing the mode of operation of the described signal processing apparatus and production of the morphology code, in accordance with an embodiment of the present invention.

A description of the mode of operation of the evaluation stage of the signal processing apparatus now follows. First of all an overview about the signal processing apparatus and the method:

Connected downstream of the input stage is an evaluation stage which in FIG. 5 is shown in the form of a diagrammatic block circuit diagram and which operates in accordance with the following method shown in FIG. 7 on the basis of a flowchart:

The method encodes/decodes signals on an event-discrete basis. The encoding specification is designed for a low level of computing performance and is optimized in a given implementation in particular for embodiment in the form of a state machine or assembler code. It is therefore possible for that encoding method to be embodied in a medical implant. The complication and expenditure is shifted to the decoding method which is also designed for the incorporation of expert knowledge (for example in the form of an expert system).

Now, described hereinafter is the encoding procedure, for the execution of which the signal processing apparatus is designed.

Figure 8:
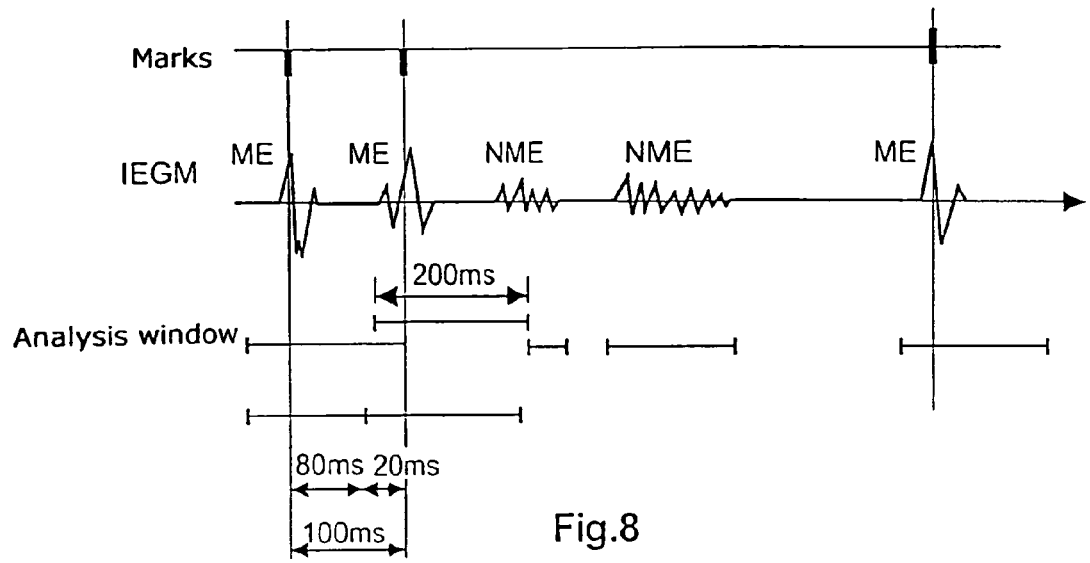
FIG. 8 shows a typical analysis window for the treatment of marker signal events (ME) and non marker signal events (NME), in accordance with an embodiment of the present invention.

A signal flowchart in respect of encoding is diagrammatically illustrated in FIG. 7. As preparation for encoding, the signal is firstly segmented. In that case a distinction is drawn between ME segments (marker event) and NME segments (non marker event). ME segments are disposed within an established time window around a reference moment in time given by a marker (specific implementation: 40 ms before same to 160 ms after same), wherein the window limits are possibly so adapted that two adjacent ME segments do not overlap (proportional curtailment in dependence on the spacing of the adjacent markers, specific implementation: division of the spacing between the adjacent markers in the ratio of 80%/20%). NME segments are to be found in the regions outside the ME windows, in which respect also a plurality of NME segments can be found between two ME windows (FIG. 8). This involves for example cardiac activities which were classified as not relevant by the sensing stage in terms of therapy control, but can diagnostically be of significance. The limits of the NME segments are determined either by an ME segment or by a signal portion which, within an established time window, is of a signal energy lower than an established value (specific implementation: time 24 ms, signal energy=0).

The zero band crossings are determined within the signal segments (ME and NME) and the extreme is respectively identified therebetween (significant signal spike in that portion, see FIG. 1). For the signal segment to be analyzed, it is assumed in this respect that it starts from the zero line and also ends on the zero line again. That method affords a sequence of signal spikes whose polarity is always alternating. It is therefore sufficient, for reconstruction purposes, for only the absolute values of the amplitudes and the polarity of a selected signal spike to be encoded.

A distinction is drawn between ME and NME for the further procedure:

Firstly, the processing of marker events (MEs) will be described.

In the case of ME a maximum number of N signal spikes is deemed to be the beginning of a segment (specifically N=5). The amplitudes of the signal spikes determined in that way are classified by way of a generally non-linear diagram (kA classes). On the basis of visual perception, in the specific implementation the amplitude classes "zero", "small" (s), "medium" (m) and "large" (l) are distinguished (that is to say kA=4). The threshold values of classification are established relative to the largest signal spike (100%) (specifically: class limits "zero"=0-12.5%, "small"=12.5-37.5%, "medium"=37.5-75% and "large"=75-100%). Those limits can be fixed or can be of a programmable nature. The amplitude A of the largest signal spike (and thus of the ME) is stored with an adequate degree of resolution (specifically 4 bits).

Among the signal spikes of the highest class (in general there can be several), that with the highest significance is determined from morphological points of view. It is also referred to as the "central signal spike". In the specific implementation, a distinction is drawn in that respect as to whether the number (ng) of the signal spikes of type g is even (ng=2n) or odd (ng=2n+1). In the odd numbered case the central one in the sublist of the g-spikes acquires the rank of the "central signal spike". In the even-numbered case, a check is made, for the signal spikes n and n+1 in the sublist of the g-spikes, to ascertain which thereof in the overall list of all N spikes being considered is closest to the middle of the list and that is then considered as central. If equality obtains, the decision is for the one which is more to the left. That ensures that as many as possible of the spikes always effectively contribute to calculation of the event code characterizing the morphology and consequently the event is described in the best possible way. The signum (S) is determined and stored for the central signal spike.

The time spacing between the first and last ones of the N spikes is also classified by way of a generally non-linear representation (kB classes). It encodes the width (W) of the event. Those limits can be fixed or programmable. In the specific implementation kB=4 classes are defined (encoding with 2 bits).

The procedure for calculation of the event code ("quantification" of the morphology) is as follows:

The amplitude classes are identified in such a way that they represent digits ($\alpha$) of a number in the base $\beta$ ($\alpha$=kA). In other words, the range of values of the digits extends from 0 to kA−1. Therefore a number is formed in the base $\beta$, wherein the positioning of the digits (that is to say the corresponding spikes) is established in accordance with their importance. The central signal spike is always of the highest level of importance. That information is redundant is accordingly does not have to be transmitted. The central signal spike is by definition of type g and its sign is already described by the signum S.

The differences between the morphologies therefore only result from the satellite spikes which surround the central one g. Let the importance of those spikes be described by way of a mapping a(i) which associates the digits (representative of the spikes) with the corresponding powers.

The event code (Ce) is accordingly a positive number in the base $\beta$ with up to N−1 significant places:

$$C_e = \sum_{i=0}^{N-2} a(i) \cdot \beta^i \quad (1)$$

A suitable choice of the mapping a(i) makes it possible to provide that events with codes which are close together are of a given morphological similarity. This provides that an order relationship is defined onto the space of the morphologies. That is a quite crucial prerequisite to provide that, even with a reduced pattern set, the entire space of the morphologies can however be completely described at least approximately in regard to the number of its elements. If no pattern whose event code exactly coincides with the calculated code is present in the reduced pattern base, the pattern whose event code differs least therefrom can be used for reconstruction.

In the specific implementation, the mapping a(i) is as follows: the satellite spikes are taken alternately from right and left of the central signal spike and associated with the powers. The procedure is started immediately to the right of the central signal spike and importance decreases with the distance therefrom. If in that respect it would be necessary to jump to positions outside N considered spikes of an ME by virtue of the specific position of the central signal spike, the corresponding coefficients in (1) are to be set equal to zero.

For the specific implementation $\beta=4$, whereby an advantageous implementation is possible in a binary system (in hardware as well as software). It is characteristic of this method that the digit 0 does not occur in the midst of the number. That is to say, the number of the possible different event codes is substantially lower than the number of all possible numbers which can be formed in the base $\beta$ with N−1 places. For the specific implementation, this means that for N=5 and kA=4, there are fewer than 256 different event codes (for $3*4^3+3*4^2+3*4^1+3=255$).

In the case of the IEGM signals, certain patterns occur substantially more frequently than others (see FIG. 2) so that rare patterns can be dispensed with, in a first approximation, in particular as the secured order relationship permits a good approximation by a different pattern. In the specific case it is appropriate for the size of the pattern base to be reduced to 32 representatives. Pattern subcodes (P) which by virtue of their smaller number can be represented on smaller word widths are associated with the event codes which are to be calculated in accordance with (1) for the patterns of the pattern base. Mapping of the event codes onto the amount of those pattern subcodes can be effected either by a computing specification based on the order relationship or by a look-up table. In that case the look-up table is programmable (that is to say it is not "fixed-wired"). Instead of the event code which is unique for a signal spike sequence, the code of the pattern is to be transmitted, which in the sense of the order relationship is most similar to the original (that is to say whose event code is closest to that of the original). This involves a lossy source encoding. By virtue of the very unequal frequencies, the use of an entropy encoding method (for example Hufmann) is also advantageous for optimized encoding (mapping of event codes onto pattern codes).

In principle this method for encoding the amplitude patterns can also be adapted for the patterns which arise out of the widths of the individual spikes. Then the spike widths are to be classified, associated with digits and calculated in a similar manner as in (1) to give a morphology subcode for the width information. Similarly to the amplitude classes provided for classification of amplitudes, width classes (kB) can be provided for classification of the spike widths, describing the relative width of an individual spike within a signal segment. The width of an individual spike can then be reconstructed because the number of the individual spikes and their relative individual spike width given by the association with one of the width classes are known and can be calculated with the total width, given by the signal width subcode, of a signal segment or an event. The morphology code is then to be supplemented by that width information. For the specific implementation of IEGM encoding, encoding of the spike widths is found not to be necessary.

The morphology code combines in a suitable succession the above-described morphological metrics of each event to be transmitted. In the case of the specific implementation the morphology code is made up as follows:

WWSPPPPPAAAA

Each of the symbols stands for 1 bit and bears the significance discussed in the text. A still further item of information which provides information about the rhythmic classification of the event can also be formally associated with that morphology code. That item of information (such as for example VT class) is generally linked in cardiotherapeutic implants to the marker (marker type M) and therefore in the specific implementation is encoded in regard to time encoding.

The method of determining the morphology code is admittedly similar to vector quantization, but it is distinguished therefrom in that it can be used for signal blocks of differing length, which is indispensable for the specific use.

There now follows a description of processing of non marker events.

Non marker events with up to N=4 spikes, in the specific implementation, are analyzed in accordance with the same procedure as marker events, but encoding associates in part a different significance with the code fields of the descriptor. Instead of the classification in regard to marker type, which is not available for NMEs, M encodes the number of spikes and for N>4 W gives subdivided into rougher classes the number of signal spikes of an NME. For NMEs which frequently represent signal components oscillating at higher frequency, a measurement in respect of frequency is also to be encoded; in the simplest implementation the binary information "faster" or "not faster", as a reference frequency.

Finally, there is, in accordance with an embodiment of the present invention, provided time encoding which is described hereinafter.

Encoding of time information is designed for the general use of a multi-channel storage/transmission situation. In that case the time in relation to the event last processed in the encoding method is always measured and encoded, irrespective of the channel in which that occurred. Later association is to be uniquely deciphered from the marker type (M). This has the advantage that the numerical values for the times to be encoded are smaller and consequently smaller word widths are required. That advantage is enjoyed in particular in respect of IEGM signals from different cardiac chambers, the events of which are predominantly time-displaced. In order to avoid an overrun in the case of long time intervals between events, the method provides an overrun code which announces a further supplementary time value. Time intervals of any length can be encoded by a plurality of successively occurring overrun codes.

The time code is made up as follows in the specific implementation:

[overrun code, . . . , overrun code], MMMTTTTT wherein each symbol stands for a respective bit of the marker type (M) and the time interval (T) respectively.

The method can operate both in the causal and also the acausal direction. The latter case presupposes that the raw data are already put into intermediate storage and it is then of interest if the previous history, that is to say the signal configuration before the occurrence of a defined trigger, is to be encoded.

The data obtained in that way for encoding of a physiological signal can be transmitted to an external device by way of a data stream. A structure of such a data stream, by way of example, is described hereinafter.

In a representation which is generally of a multi-channel mixed nature the data stream represents a succession of time and morphology data, wherein the morphological descriptors are optional.

In the case of the specific implementation morphological descriptors are encoded only for the ventricular IEGM signals while the atrial data are restricted to rhythmological information. Whether a morphological descriptor follows an item of (obligatory) time information, can be seen from the marker type which is always a constituent part of the time information. Basically, in the specific implementation, the data stream is begun with an item of time information, to ensure unambiguity.

Such a data stream can be received by an external device and there again converted into a representation of a physiological signal. For that purpose the external device is adapted to reconstruct the data stream as follows.

The reconstruction method follows the description of the data stream structure. An example with different case distinctions as to how a data stream is deciphered in the specific implementation is illustrated in FIG. 11.

In the example shown in FIG. 11 the morphology code data stream 41006CA5022A4ACBA1FCA... is decoded and thus the encoded intracardiac electrocardiogram is reconstructed.

The sequence of time (8 bits) and morphology values (12 bits) includes a total of 47 bytes:

IEGM:=cardiac action [cardiac action . . . ]
Cardiac action:=time (V-morphology)
Time:=time byte [time byte . . . ]

The sequence always starts with a time byte. Reconstruction starts at the detection mark (this is not transmitted) in the direction of the past, that is to say the first time value reflects the distance relative to the detection mark. A time byte is of the following 8-bit structure with marker bits (M) and time bits (T):

MMMTTTTT

In the time byte the significances are as follows:
TTTTT<0x1F: a time value in steps of 1/64 s, that is to say how far the current marker is back before the last reconstructed one, and TTTTT==0x1F: the time byte is to be interpreted as a special character.

The marker bits (MMM) mean as follows:

000: Vs

001: VT1

010: VT2

011: VF

100: SVT

101: Vp

110: As

111: Ap

The special characters mean as follows:
0x1F: time overrun, time bytes follow until TTTTT<0x1F
total time value=[(number_time bytes−1)*0x1F+ TTTTT(<0x1F)]*(1/64 s)
0x3F: end of the IEGM V-data
0x5F: end of the IEGM A-data The morphology code data stream is to be read from left to right and gives an electrocardiogram which is to be read from right to left.

Figure 9:
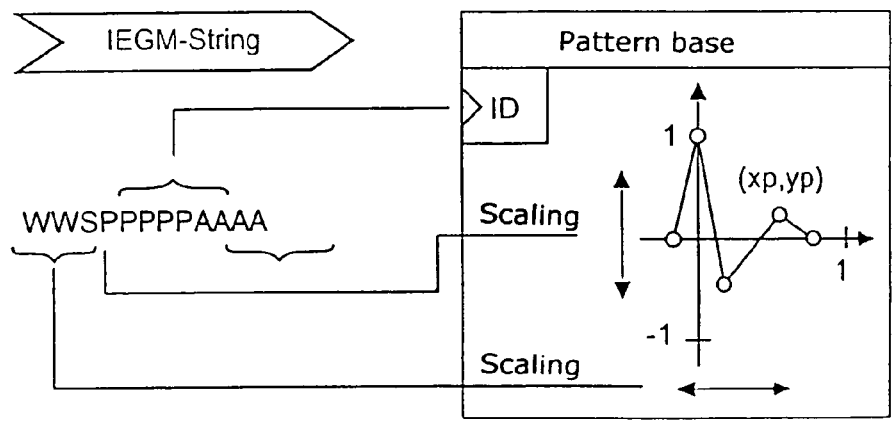
FIG. 9 is a representation of the reconstruction of the morphology of an electrocardiogram from the morphology code, in accordance with an embodiment of the present invention.

For graphical (approximate) reconstruction of the signal configurations of an event, the corresponding graphical pattern is taken from the pattern base by means of the pattern code (P) transmitted in the morphological descriptor. In the pattern base, the patterns are represented in standardized form both in terms of the amplitude axis and also the time axis. That pattern is then scaled in accordance with the specification of the morphological descriptor and more specifically SAAAA stretches or compresses the amplitude axis (including polarity reconstruction) and WW stretches or compresses the time axis (FIG. 9). In that way an approximation for the original event (signal segment) is produced from the neutral pattern. A crucial advantage over correlation-based pattern analyses (for example correlation waveform analysis (CWA)) lies in the scalability of the pattern along the time axis. The wavelet transformation method would admittedly also enjoy that advantage, but the latter is however substantially more complicated and expensive to execute than the method set forth herein.

The width ratios of the individual spikes are taken from the pattern base. For the specific implementation, they were determined in a representative study on a heuristic basis for each of the individual patterns. If the procedure involves encoding in analogous manner with the amplitude patterns, decoding of the width ratios is to be effected in a similar manner.

The patterns are strung together in a row in accordance with their time sequence. Possible overlap conflicts as a consequence of the finitely accurately classified time and width information which only permits a limitedly accurate reconstruction are resolved by compression (as demonstrated in Appendix 1) or by fusion of adjacent events. Context-dependent corrections (for example typical latency times are involved in the case of stimulated events) can be effected by suitable reconstruction rules (for example by way of an expert system).

FIG. 10 by reference to an example shows the comparison between reconstruction and the original signal. The reconstructed signal is available for example in a home monitoring service center (HMSC).

Terminology

Cardiac event: signal portion with above-threshold signal energy, generally a portion of the period of a measurement signal which is quasi-periodic (for example pulsating in the cardiac rhythm) (for example the QRS complex);

Event sequence: chronologically successive individual events;

Marker event (ME): event within a defined window around a maker;

Non marker event (NME): cardiac activity outside the ME windows;

Zero band crossing: the zero band extends over an amplitude range of +/−delta around the zero line. A zero band crossing occurs if the signal configuration changes from values quantitatively larger than delta of a given polarity to values quantitatively larger than delta of the opposite polarity. A zero band crossing in contrast does not occur if the signal only dips into the zero band, even if the polarity changes in that case.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A signal processing apparatus, said apparatus comprising:
an input stage configured of receive a time-varying physiological signal having a morphology that changes over time, and configured of operate on said time-varying physiological signal to generate an evaluable time-varying signal having an alternating polarity;

an evaluation stage operatively connected to said input stage, said evaluation stage configured to respond to a reference moment in time and configured to receive said evaluable time-varying signal; and an output stage operatively connected to said evaluation stage, wherein said evaluation stage comprises a zero-crossing detector, a curve point detector, and a maximum/minimum detector, wherein said zero crossing detector is configured to detect zero crossings in at least one signal segment of said evaluable time-varying signal and determining a time of occurrence of said zero crossings with respect to said reference moment in time, and wherein said curve point detector is configured to detect curve points between neighboring zero crossings in said at least one signal segment of said evaluable time-varying signal, said curve points either representing magnitudes of said evaluable time-varying signal or inflection points of said evaluable time-varying signal, or both, between said neighboring zero crossings, and said curve point detector being further configured to determine a time of occurrence of said curve points with respect to said reference moment in time and an amplitude of said evaluable time-varying signal at said curve points, and wherein said maximum/minimum detector is configured to operate on said evaluable time-varying signal to determine a largest magnitude of said evaluable time-varying signal within said at least one signal segment, and wherein said evaluation stage is further configured to generate a morphology code, wherein said morphology code comprises a pattern subcode that represents a pattern of said magnitudes of said evaluable time-varying signal at said curve points relative to said largest magnitude of said evaluable time-varying signal within said at least one signal segment, and wherein said morphology code further comprises an amplitude subcode that represents said largest magnitude of said evaluable time-varying signal within said at least one signal segment.

2. The signal processing apparatus as set forth in claim 1 wherein said reference moment in time is a time of occurrence of a physiological event reflected in said time varying physiological signal.

3. The signal processing apparatus as set forth in claim 2 wherein said time varying physiological signal is an electrocardiogram signal and wherein said reference moment in time is a ventricular event, reflected by an R spike in said electrocardiogram signal.

4. The signal processing apparatus as set forth in claim 3 further comprising a marker signal generator, wherein said the marker signal generator is adapted to evaluate the physiological signal and to generate a marker signal upon occurrence of a ventricular event.

5. The signal processing apparatus as set forth in claim 1 wherein the evaluation stage is adapted to segment-wise evaluate the evaluable signal wherein a respective signal segment of said at least one signal segment includes a period of time beginning prior to said reference moment in time and ending after said reference moment in time, wherein the period of time is established in such a way that it is shorter than a time duration between two said successive reference moments in time so that adjacent signal segments of said at least one signal segment do not overlap.

6. The signal processing apparatus as set forth in claim 5 wherein the input stage or the evaluation stage is adapted to segment the physiological signal.

7. The signal processing apparatus as set forth in claim 1 wherein the evaluation stage is adapted to generate said morphology code for each of said at least one signal segment in dependence on the evaluable time varying signal for said respective signal segment.

8. The signal processing apparatus as set forth in claim 1 wherein the evaluation stage is adapted, for generating said pattern subcode, to classify characteristic values of said curve points or at least the relative amplitudes of the signal maxima and minima in accordance with their relative magnitude in relation to a reference signal amplitude in a limited number of amplitude classes, wherein said pattern subcode can assume a predetermined number of values, each value corresponding to one of said amplitude classes.

9. The signal processing apparatus as set forth in claim 8 wherein the evaluation stage is adapted to determine the association of the amplitude of a signal maximum and minimum with one of said amplitude classes in dependence on whether the respective amplitude of a signal maximum or minimum in relation to said reference signal amplitude is similarly large, smaller than said signal amplitude but larger than a first threshold, smaller than the first threshold but larger than a second threshold, or smaller than the second threshold.

10. The signal processing apparatus as set forth in claim 9 wherein the evaluation stage is adapted to generate an event code wherein the event code, for each signal maximum and minimum, includes an amplitude digit ($\alpha$) wherein the amplitude digit can assume one of four values corresponding to the number of amplitude classes, and wherein the event code uniquely describes the association of the respective signal maximum or minimum with one of the amplitude classes.

11. The signal processing apparatus as set forth in claim 10 wherein the evaluation stage is adapted to form the event code wherein the event code contains up to four amplitude digits wherein the four amplitude digits respectively represent the amplitude of four signal maxima or minima adjacent to said reference signal to the left and/or the right, within said respective signal segment.

12. The signal processing apparatus as set forth in claim 11 further including a look-up table wherein said evaluation stage is adapted to form said pattern subcode from said event code, by one or more event codes being associated with a pattern subcode value by way of said look-up table.

13. The signal processing apparatus as set forth in claim 8 wherein the evaluation stage is adapted to determine an absolute signal maximum or minimum within each of said at least one signal segment and to use the corresponding signal value as said reference signal amplitude.

14. The signal processing apparatus as set forth in claim 8 wherein the evaluation stage is adapted to determine the magnitude of an R spike in said physiological signal and to use said R spike magnitude as said reference signal amplitude.

15. The signal processing apparatus as set forth in claim 1 wherein said pattern subcode includes a sign digit (S) whereby the sign digit represents the sign of a reference signal amplitude.

16. The signal processing apparatus as set forth in claim 1 wherein said morphology code further includes a signal width subcode (WW).

17. The signal processing apparatus as set forth in claim 16 wherein said signal width subcode (WW) represents either a time spacing between a first signal maximum or minimum and a last signal maximum or minimum within said at least one signal segment or the duration of the at least one signal segment.

18. The signal processing apparatus as set forth in claim 1 wherein said amplitude subcode forms a scaling factor and whereby the scaling factor represents a reference signal amplitude as an absolute value.

19. The signal processing apparatus as set forth in claim 1 wherein the morphology code is a binary code having one or more of the following constituents:
   a signal width subcode (WW) wherein the signal width subcode includes at least two binary digits,
   a sign subcode (S) comprising a binary digit,
   said pattern subcode (PPPPP) wherein the pattern subcode includes at least five binary digits, and
   said amplitude subcode (AAAA) wherein the amplitude subcode includes at least four binary digits.

20. The signal processing apparatus as set forth in claim 1 wherein the evaluation unit is adapted to associate a time code with said morphology code and to add the time code with the morphology code.

21. The signal processing apparatus as set forth in claim 1 wherein the input stage comprises a band pass filter whereby said band pass filter is adapted to produce a differentiated signal, wherein said differentiated signal is evaluated against the physiological signal.

22. An implantable electromedical device, including a cardiac pacemaker, comprising the signal processing apparatus of claim 1.

* * * * *

UNITED STATES PATENT AND TRADEMARK OFFICE
CERTIFICATE OF CORRECTION

PATENT NO.        : 7,764,987 B2                                          Page 1 of 1
APPLICATION NO.   : 11/218303
DATED             : July 27, 2010
INVENTOR(S)       : Thomas Dörr, Ingo Weiss and Peter Schneider It is certified that error appears in the above-identified patent and that said Letters Patent is hereby corrected as shown below:

Col. 14, Claim 1, line 63
replace "configured of receive"
with --configure to receive--.

Col. 14, Claim 1, line 65
replace "configured of operate"
with --configured to operate--.

Col. 15, Claim 4, line 54
remove "said".

Signed and Sealed this

Fifth Day of October, 2010

David J. Kappos
*Director of the United States Patent and Trademark Office*